(12) United States Patent
Huang et al.

(10) Patent No.: US 10,240,723 B2
(45) Date of Patent: Mar. 26, 2019

(54) DIGITAL REGULATED GAS DISPENSING APPARATUS WITH A MEMS MASS FLOW METER

(71) Applicants: Liji Huang, San Jose, CA (US); Chih-Chang Chen, Cupertino, CA (US)

(72) Inventors: Liji Huang, San Jose, CA (US); Chih-Chang Chen, Cupertino, CA (US)

(73) Assignee: Siargo Ltd., Santa Clara, CA (US)

( * ) Notice: Subject to any disclaimer, the term of this patent is extended or adjusted under 35 U.S.C. 154(b) by 113 days.

(21) Appl. No.: 15/609,518

(22) Filed: May 31, 2017

(65) Prior Publication Data

US 2018/0347759 A1 Dec. 6, 2018

(51) Int. Cl.
*F17C 13/02* (2006.01)
*F17C 13/04* (2006.01)
*G01F 1/684* (2006.01)
*G01F 1/696* (2006.01)
(Continued)

(52) U.S. Cl.
CPC ......... *F17C 13/02* (2013.01); *A61M 16/1005* (2014.02); *A61M 16/16* (2013.01);
(Continued)

(58) Field of Classification Search
CPC .... F17C 13/02; F17C 13/04; F17C 2250/034; F17C 2270/025; F17C 2265/06; F17C 2250/0495; F17C 2250/0491; F17C 2250/0426; F17C 2250/0443; F17C 2250/032; F17C 2221/011; F17C 2205/0329; F17C 2205/0338; F17C 2201/032; F17C 2201/0109; F17C 2270/05; A61M 16/16; A61M 16/1005; A61M 2205/50; A61M 2205/3334; A61M 2205/0244; A61M 2202/0208; A61M 2016/0033; A61M 2205/3584; G01F 1/696; G01F 1/6845

See application file for complete search history.

(56) References Cited

U.S. PATENT DOCUMENTS 4,916,437 A * 4/1990 Gazzaz .................... F17D 5/02
251/129.01
5,908,980 A * 6/1999 Hwang ............... G01M 3/2815
137/557

(Continued)

*Primary Examiner* — David P Angwin
*Assistant Examiner* — Bob Zadeh

(57) ABSTRACT

The design and structure of a regulated digital gas dispense apparatus is exhibited in this disclosure. The MEMS mass flow meter embedded with a Bluetooth communication device and powered by a battery pack is designed to replace the mechanical low pressure gauge in a conventional gas dispense regulator such that the dispensed gas flowrate as well as totalized dispensed gas volume in each session or in consequent sessions can be continuously and precisely registered. The measured data are further relayed to local users via the local display or physical data port as well as via a paired smart device running a customized APP that can further relay the data to a designated cloud for cloud data processing, and the data can be streamed reversely. This disclosure shall assist and realize the ultimate optimized management for the users, distributors and/or gas manufacturers in the gas dispensing industry.

14 Claims, 12 Drawing Sheets

(51) Int. Cl.
*A61M 16/10* (2006.01)
*A61M 16/16* (2006.01)
*A61M 16/00* (2006.01)

(52) U.S. Cl.
CPC ............ *F17C 13/04* (2013.01); *G01F 1/6845* (2013.01); *G01F 1/696* (2013.01); *A61M 2016/0033* (2013.01); *A61M 2202/0208* (2013.01); *A61M 2205/0244* (2013.01); *A61M 2205/3334* (2013.01); *A61M 2205/3584* (2013.01); *A61M 2205/50* (2013.01); *F17C 2201/0109* (2013.01); *F17C 2201/032* (2013.01); *F17C 2205/0329* (2013.01); *F17C 2205/0338* (2013.01); *F17C 2221/011* (2013.01); *F17C 2250/032* (2013.01); *F17C 2250/034* (2013.01); *F17C 2250/0426* (2013.01); *F17C 2250/0443* (2013.01); *F17C 2250/0491* (2013.01); *F17C 2250/0495* (2013.01); *F17C 2265/06* (2013.01); *F17C 2270/025* (2013.01); *F17C 2270/05* (2013.01)

(56) References Cited

U.S. PATENT DOCUMENTS

| | | | | |
|---|---|---|---|---|
| 6,142,149 A * | 11/2000 | Steen | ............... | A61M 16/00 128/204.21 |
| 6,394,088 B1 * | 5/2002 | Frye | ............... | A61M 16/20 128/204.26 |
| 8,342,018 B2 * | 1/2013 | Huang | ............... | G01F 1/6845 73/204.26 |
| 8,869,822 B2 * | 10/2014 | Boyer | ............... | F17C 13/04 137/377 |
| 8,994,552 B2 * | 3/2015 | Jiang | ............... | H04Q 9/00 340/870.02 |
| 9,435,675 B2 * | 9/2016 | Wise | ............... | G01F 15/0755 |
| 9,752,783 B2 * | 9/2017 | Huang | ............... | F24C 3/126 |
| 9,784,607 B2 * | 10/2017 | Wong | ............... | G01F 1/78 |
| 2006/0266228 A1 * | 11/2006 | Ritterling | ............... | A47J 37/067 99/450 |
| 2012/0019378 A1 * | 1/2012 | Watson | ............... | H04L 12/2825 340/539.1 |
| 2012/0024054 A1 * | 2/2012 | Huang | ............... | G01F 1/6845 73/204.26 |
| 2013/0201316 A1 * | 8/2013 | Binder | ............... | H04L 67/12 348/77 |
| 2013/0260320 A1 * | 10/2013 | Townsend | ............... | F24C 7/08 431/2 |
| 2014/0116129 A1 * | 5/2014 | Yang | ............... | G01F 1/6845 73/204.22 |
| 2014/0159877 A1 * | 6/2014 | Huang | ............... | G08C 17/02 340/12.5 |
| 2018/0347759 A1 * | 12/2018 | Huang | ............... | F17C 13/02 |
| 2018/0348030 A1 * | 12/2018 | Chen | ............... | G01F 1/6847 |

* cited by examiner

DIGITAL REGULATED GAS DISPENSING APPARATUS WITH A MEMS MASS FLOW METER

BACKGROUND OF THE INVENTION

1. Field of the Invention

This invention generally relates to fluid flow measurement, and it particularly relates to a flow measurement apparatus that utilizes micro-electro mechanical system (MEMS) mass flow sensing technology to meter the gas dispensing and consumption in medical, consumer and general purpose industrial applications. This invention is further related to internet of things (IOT) that connect multiple devices and relay such information to the cloud computing in the ease of management and cost reduction.

2. Description of the Related Art

Gas dispensing and consumption are among the most common applications in gas metering. For example, oxygen dispensing to patients at hospital or to consumers in the form of home care; gas dispensing for instrumentation in laboratory and bottled special as, dispensing at industrial process lines. For industrial applications, there are millions of gas bottles or cylinder delivered daily worldwide. Up to date, each of those gas bottles or cylinders has a pressure sensor to monitor the gas consumption via the pressure rate inside the bottle and a gas flow meter made by variable area technology (floater or rotameter) to control the gas dispensing. While these kinds of devices are cost effective, they are far inaccurate for the metering of the accurate gas consumption or remaining volume of the gas inside the gas bottle. The pressure sensor is a mechanical one having a short dynamic range and full scale accuracy while the rotameter is also made by a mechanical approach with a fall scale pure volume output that is often affected by the variation of the environmental temperature and gas pressure. The inaccuracy would lead to difficulties in gas management and in most cases to huge waste of the gas in particular for the special gases used in industrial process. Further, it would also lead to loss of efficiency in work process if the gas consumption is under estimated. On the other hand, over estimation shall add unspecified cost to the gas consuming party. In some specific cases for the medical oxygen gas home care applications, the manufacture is often unprepared for the timely delivery of the gas bottle as no knowledge of the consumption of the oxygen can be registered in the controllable approach, and the manufacturers have to keep a huge inventory as for the varieties of the bottle capacities and consumption pattern, leading to the high cost of the manufacture and inventory management which is finally born to the users.

A typical as dispensing system has a gas container or a gas bottle in which the gas is highly pressurized. A gas dispense apparatus usually is installed on the gas container or gas bottle before the as dispense or delivery can be executed. The apparatus for the gas dispenser or container normally has a high pressure gauge that measures the pressure inside the gas container and another low pressure gauge that measures the pressure data in the dispensing or delivery line while a pressure regulating valve is placed at the middle of the two pressure gauges. These two pressure gauges are normally of pure mechanical type and insensitive to the full dynamic range of the gas to be dispensed. An example taught in the prior art in attempt for an improvement of the gas dispense for human oxygen dispensing (Steen, S. K., Oximetry device, open oxygen delivery system oximetry device and method of controlling oxygen system, U.S. Pat. No. 6,142,149, Nov. 7, 2000) shown a system that coupled with an oxygen saturation sensor and a flow sensor with a manual valve such that the oxygen information can be relayed for future reference. Such device still does not have the capability to alter the user in case the oxygen is completely consumed with risks at sudden cut-off of the gas supply from the gas bottle. A similar system disclosed by Frye, M. R. et al. (Frys, M. R., Brown, J. F. and Leithauser, D. R., Oxygen-delivery system with portable oxygen meter, U.S. Pat. No. 6,394,088, May 28, 2002) also does not have the capability to metering the oxygen consumption but a control function by the metering system.

Metering a gas container such as a tank or bottle is traditionally achieved via a weight station or similar weight devices or, in case of the form of a liquid under high pressure, a level sensor device that can be used to monitoring the remaining of the gas in the container (Northrop, C. L., Tank mass measurement assembly, U.S. Patent Application 2006/0130572, Jun. 22, 2006). Cohen, J. P. et al., (Cohen, Mattiola P. A. and Farese, D. J., Process for filling compressed gas fuel dispensers which utilizes volume and density calculation, U.S. Pat. No. 6,708,573, Mar. 23, 2004) taught a device that involved a complicated process to measure the volume, pressure and temperature of a pressurized fluid followed by consequently calculation that shall finally determine the mass values of the gas container. In a most recent disclosure (Wise, E. C., Method and apparatus for monitoring, communicating and analyzing the amount of fluid in a tank, U.S. Pat. No. 9,435,675, Sep. 6, 2016), a special device is proposed to monitor the remaining mass contain of a gas container. Inside the special device a flow meter is used to measure a plurality of flowrates that vary when being dispensed, and the embedded processor shall be used to determine the remaining mass and an indication shall then be generated by the device. However, the disclosed device for the gas consumption is based on the a rolling mean or average of a plurality of non-continuous measured flow rate that may be quite deviated from the actual mass as it also requires the knowledge of the gas density, pressure and temperature. The disclosed device has a capability to be remotely connected to a system comprised of a robot and a software application for the remote gas data management. While this does provide values to the management of the logistics of the gas bottles or cylinders, the actual user(s) of the gas containers are left out of the cycle as the user(s) must only be at the promise close to the gas containers in order to have the knowledge of the status of the gas bottles or cylinders which does not provide sufficient benefits for the actual user(s). In addition, this device is an additional unit, if direct attached to the high pressurized gas container, may have some safety risks and each pressurized gas container shall equipped with dual durable mechanical pressure gauge together with a pressure regulation mechanical valve that ensures the gas released from the pressurized container would not risk the applications. Attachment of the gas regulation valve before or after the disclosed device shall add excessive part which makes the operational inconvenient while the disclosed device shall also require external power source which adds other operational difficulties.

SUMMARY OF THE INVENTION

It is therefore the objective of the present disclosure to provide the design of a apparatus and the corresponding system that shall be used to seamlessly replace the current mechanical apparatus with added features that shall allow the user as well as the manufacturer of the as containers or bottles or cylinders to be beneficial from such a system such that the management of the usage of the gas in a container either for industrial or medical or domestic applications can be efficient, the desired data can be measured directly and accurately without additional information or excessive calculation required, and further the cost of the current management scheme shall be significantly lower. The said device as well as the system shall also not add any addition parts but a direct replacement of the current pure mechanical apparatus without losing any advantageous features of the system, in particular of the safety features. The device shall be stand-alone with the ability to be wirelessly interacting with the smart devices such as a smart phone that are at reach by the users at any time that the smart devices can be further communicating with the destined cloud for data process or computing that relays to the bottled gas manufacturer for inventory and manufacture management in a more efficient arrangement.

In one preferred embodiment, the disclosed apparatus shall have the said MEMS mass flow meter for metrology of the gas dispensing and relay the information to the user as well as the manufacturer via cloud data process. The said MEMS mass flow meter shall be powered by battery as a stand-alone unit with the MEMS mass flow sensor for direct measurement of the gas consumption to replace the low pressure gauge in the mechanical apparatus of gas regulator for gas bottles or cylinders Or containers while the mechanical pressure regulating valve and high pressure mechanical gauge sensor for monitoring the pressure inside the gas bottles or cylinders/containers shall be kept unchanged. The said MEMS mass flow meter shall directly and continuously measure the totalized gas being dispensed without the necessity for additional temperature and pressure measurement and averaging the plurality of the flowrates being registered. Instead of using the mechanical pressure gauge to monitor the dispensing gas outflow, the said MEMS mass flow meter shall display both the instant flowrate and the totalized flow such that the status of the dispensing line shall be more precisely registered as the said mass flow meter is far sensitive to the gas status as compared to the readings with the current mechanical gauge sensor. The said MEMS mass flow meter shall further have the memory in the form of electronic flash that shall register the total dispensed volume of gas in each session that can be pre-set by the user and alter shall be sent to the user if the pre-set value were reached. The total consumed gas shall be further added up by the values at each session and such information can be timely relay to the user or be retrieved upon user enquiries. The said MEMS mass flow meter further have the integrated gas recognition sensor that shall be operated in thermal conductivity metrology principle which can further relay the information to the user in case the gas type being dispensed shall not be the desired one.

In another preferred embodiment, the disclosed apparatus shall have the said MEMS mass flow meter for metrology of the gas dispensing and relay the information to the user as well as the manufacturer via cloud data process. The said MEMS mass flow meter as the new key metrology and data acquisition device replacing the low pressure mechanical gauge shall be in the format of a tiny cylinder with a LCD or LED or OLED display. In such an arrangement similar to a mechanical rotameter which from time to time used as a flow monitor. The complete flow channels and the corresponding sensing electronics shall be embedded inside the cylinder configuration that shall be compatible with the most of the current pressure regulators with safety for the gas bottle/container dispensers via the connection at the bottom or the base of the cylinder formality. The base for the cylinder formed MEMS mass flow meter can be made completely with metals having the desired thread identical to that of the low pressure gauge for the corresponding pressure regulators. The metal base of the mass flow meter can also be made alternatively in variety of formalities with single or plurality of the inlet/outlet gas dispensing ports that shall be compatible with the varieties of the gas dispenser models.

In another preferred embodiment, the disclosed apparatus shall have the said MEMS mass flow meter for metrology of the gas dispensing and relay the information to the user as well as the manufacturer via cloud data process. The said MEMS mass flow meter shall have its flow channels for measurement of the dispensed gas in an assembly that shall be composed of plurality number of channels that evenly distributed in a circular formality. As such the MEMS flow sensor chip shall only be required to be placed in one of the channels that shall have an adjustable channel size M accordance with the maximum flowrate to be measured. This configuration shall allow the flexibility of the MEMS mass flow meter configuration that shall be matched to the variety of the gas regulator for the gas bottles or cylinders for the different applications or purpose. Thereafter, the full scale of the said MEMS mass flow meter can be adjusted via the changes of the sensor assembly that shall be very cost effective and easy for inventory management per the vast varieties of the gas containers in particular with respect to their capacity that shall require mass flow meters with different full scales.

In another, preferred embodiment, the disclosed apparatus shall have the said MEMS mass flow meter for metrology of the gas dispensing and relay the information to the user as well as the manufacturer via cloud data process. The assembled stand-alone battery powered MEMS mass flow meter shall be further connected to the traditional gas regulating apparatus by replacing the lower pressure gauge to formulate a new regulated digital gas dispense apparatus which shall have the said functionality of continuously metering the dispensed gas and relaying such information to the user via the connectivity to a smart device and further to the cloud for the assistance of the management to the manufacturer. The said new gas regulating apparatus shall be readily connected to any gas bottles or cylinders/containers. In a preferred circumstance, the said new gas regulating apparatus shall also be utilized in other applications where gas bottles or cylinders/containers are replaced by a fixed gas source or gas generator whilst the gas dispensing information is also crucial to the users or the applications. Specifically, in a medical oxygen dispense to patient, the inhalation of oxygen gas by patient is being considered a therapy process, excessive or insufficient dispensing or delivery shall all be detrimental where the said gas regulating apparatus with the MEMS mass flow meter shall effectively remove such obstacles.

In yet another preferred embodiment, the disclosed apparatus with the MEMS mass flow meter to replace the low pressrun gauge of the gas regulator for gas container/bottle dispensers. The said MEMS mass flow meter shall anther have the low energy version of Bluetooth communication components embedded inside the said MEMS mass flow meter electronics. With this preferred configuration, the gas dispensing data acquired by the said MEMS mass flow meter can be readily transmitted to smart devices such as a smart phone or a tablet that is widely available or accessible for the relevant user. The software designated to be run on smart devices or the APP shall be used for further data logger and/or analysis for the interactive information of the gas status inside the bottle or the container. Alternatively the data registered in the said MEMS mass flow meter can also be downloaded to the smart devices via a data port such as a USB data ports in case the wireless communication has deficit. Either the APP or the data connection via the data port shall also allow the user to program the said MEMS mass flow meter such that additional functions such as gas dispense volume alarm or other parameters can be customized. In an additional preferred arrangement, the smart device shall further relay the data to or receive the instructions from the designated Cloud that have hosted the database for desired gas containers or bottles or cylinders. The bottled gas manufacture shall then be able to manage efficiently the manufacture schedule and inventory via the Cloud. This shall be particularly important for the medical gas for assistance in life-threatening theses homecare as well as the expensive manufacture gas processing lines.

The present disclosure provides a new design of a gas regulating apparatus where the mechanical low pressure gauge is replaced with a MEMS mass flow meter that shall be capable of continuously and precisely metering the gas dispense or delivery to the applications while relaying such data to the user and further to the other interest parties such as bottled gas manufacturer. These and other objectives of the present disclosure shall become readily apparent upon further review of the following drawings and specifications. And additionally for those with the knowledge of the art, the regulated digital gas dispense apparatus could be further utilized for gas delivery metering or dispensing via a fixed gas sources or a gas generator.

BRIEF DESCRIPTIONS OF THE DRAWINGS

DETAILED DESCRIPTION OF THE PREFERRED EMBODIMENTS

For either medical or industrial gas dispensing from a bottle or cylinder or a container or a fixed gas supply, a gas regulating apparatus is a necessary and critical device for a safety dispensing process. Such an apparatus is often made with a pressure regulating valve and mechanical pressure gauges to monitor the pressure inside the gas container and at the outlet of the dispensing line (e.g. Boyer, R. A., Gas pressure regulator having energy absorbing features, U.S. Pat. No. 8,869,822, Oct. 28, 2014). As the gas dispensing pattern is solely dependent on the applications and demands, the speed and volume of dispensed gas would have vast varieties, leading to difficulties for user to predicate the schedule of a timely order of a replacement, and also in particular for manufacturers to manage the manufacture and inventory. These are very much undesired for both users and manufacturers for a timely access to the status of the gas containers in the field where multiple applications would apply. Therefore, the said disclosure shall address these and all the management demands for the dispensing demands from a gas bottle or a cylinder or a container.

Figure 1A:
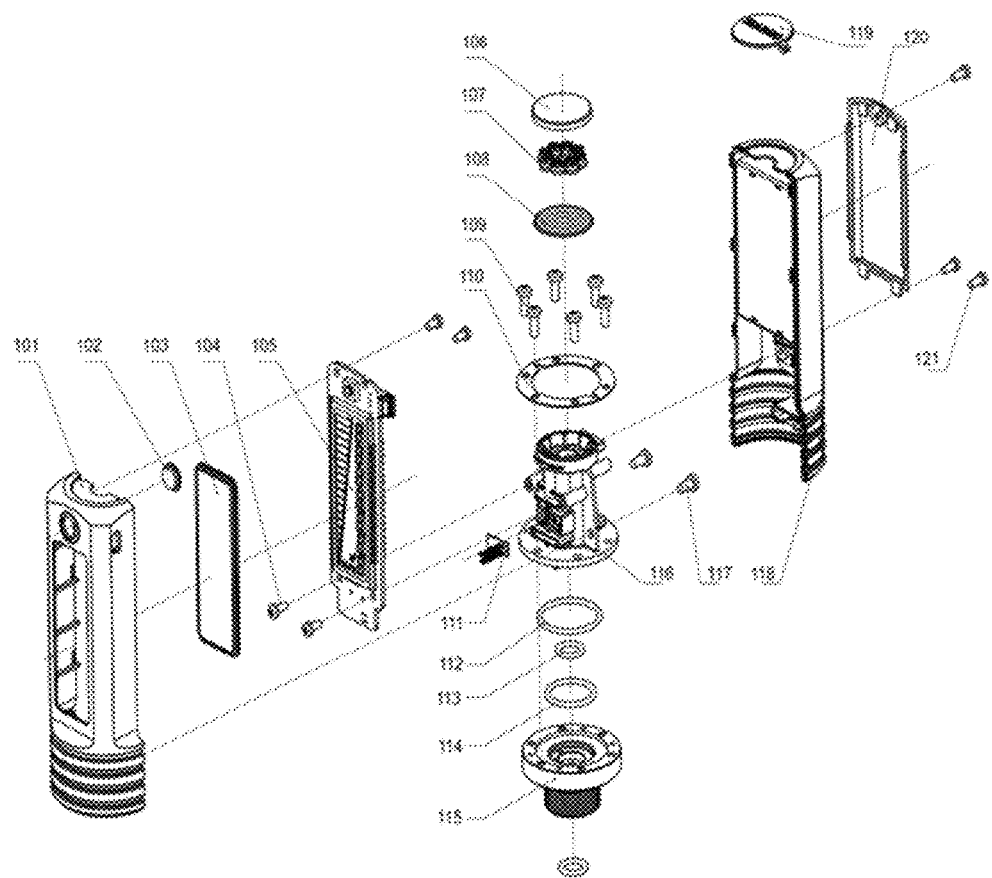
FIG. 1A is the explosive view of the MEMS mass flow meter disclosed for the replacement of the mechanical low pressure gauge in a gas regulating apparatus fanning a digitally connected device that shall be capable of communicating with user as well as the third party of interest.

For the preferred embodiment, the present disclosure of a regulated digital gas dispense apparatus for the gas dispensing management shall have a MEMS mass flow meter to replace one of the conventional mechanical pressure gauge such that the gas dispensing can be continuously and precisely metered and the data shall be relayed to both user via smart devices and manufacture via cloud data process. The explosive view of the said MEMS mass flow meter is shown in FIG. 1A, where each component of the mass flow meter is disclosed. The front cover 101 shall be made with metal or fiber enhanced or other plastic materials for sturdy protection in the applicable environments 102 is the accessible button that shall be directly in contact to the functional button on the control electronics (105). This component (101) shall be made with plastic or metal that is used for alternatively display of the instant gas dispensing flow rate and totalized dispensing volume. It shall also be used for switch on/off the said MEMS mass flow meter power for the ultimate power saving in case the apparatus shall be idle for some excessive time period. The another functions such as setting up the gas dispensing alarm limit, enable/disable the Bluetooth wireless data transmission and meter access password shall also be executed via this button in case the smart device that connected to the said MEMS mass flow meter is not readily available or at the proximity. 103 is the display protection that shall be made of transparent light plastics. 104 is the screw used to fix the display and control electronics (105) to the meter body/gas dispensing flowrate sensing unit, 116. 105 is the central control unit of the said MEMS mass flow meter, which contains the LCD or OLED display with the micro-processor unit (MCU) and signal conditioning circuitry for the MEMS sensor chip using components such as analog to digital convertor (ADC), amplifiers and other necessary electronics components. The Bluetooth wireless communication chip as well as the antenna are also part of the central electronic control unit 105. In addition, at least two physical memory chips such as e-flash are also installed on this unit with direct access by the MCU for data storage and data safety. A physical data port in the form of a micro-USB or mini-USB or USB-C is also included for access to the data on board in case the wireless data access is being disabled or not readily accessible. 106 through 110 are components of the gas dispensing flowrate sensing unit 116. 106 is the upper cover of the unit and 107 is the flow channel sealing enclosure under which is the flow conditioning component 108. 109 are multiple screws that are used to fix the flow sensing unit onto the base (115) of the said MEMS mass flow meter and 110 is the gasket for additional assistance to the fixture. 111 is the MEMS sensor chip assembly that provide the flowrate measurement via the MEMS sensing chip that utilizes the calorimetric or time-of-flight thermal mass flow sensing principle as disclosed previously by the present inventors. The sensing chip is preferred to be operated with the calorimetric mass flow sensing as no additional pressure and temperature sensing shall be required to directly metering the gas mass dispensing. An integrated thermal conductivity sensor on the same MEMS sensing chip can be used to identify the gas composition such that if an undesired gas component were present in the gas dispensing line, the sensing unit shall also be able to send an alert to the users. 112, 113 and 114 are 3 O-rings or gaskets consequently to be placed onto the base under the gas dispensing flow rate sensing unit 116 to ensure a tight leakage free sealing as some industrial gases may be hazardous to the environment. 117 are multiple screws that are used to attach and fix the front cover to the gas dispensing flow rate sensing unit (116). 118 is the back cover of the said MEMS mass flow meter, which also contains the battery pack compartment. 119 is a meter body upper fixture that also contains the logo or trade mark of the said product. 120 is the battery pack chamber cover and 121 are multiple screws that are used to additionally tighten the meter body front and back cover.

Figure 1B:
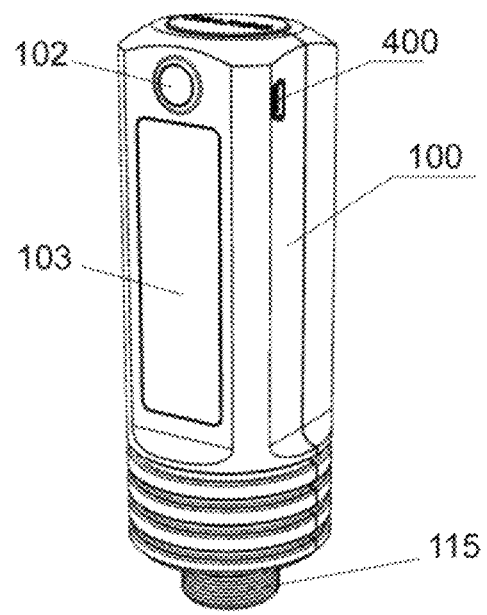
FIG. 1B is the full assembled MEMS mass flow meter that is powered by battery with Bluetooth low energy data communication and a local data port for manual data interface.

FIG. 1B exhibits the assembled stand-alone MEMS mass flow meter, 100. In the preferred embodiment, the said mass flow meter shall be operated on battery pack that is installed inside the assembled meter that shall continuously and precisely to the custody transfer standard measure the instant mass flow rate of the gas media flow through the sensing unit while totalize instantly the volume of the gas being dispensed. The data shall be stored safety and separate in a plurality of physical memory chips for ultimate data safety. Upon request the data shall be timely relayed to the user via the Bluetooth wireless communication to a smart device that shall further upload the received data seamlessly to the cloud for cloud data process which shall be accessible by the gas manufacturers. The display 103 shall instantly provide the local data streaming to the user at the proximity while the user shall be able to set the desired gas dispensing options, such as total dispense limit, maximum or minimal dispensing flow rates, and/or time of dispensing via the APP of a smart device that is connected to the said MEMS mass flow meter or the physical button 102 on the said meter. Alternatively, the user can also download the data or program the meter in the physical user interface 400, preferably in the format of a USB port such as micro- or mini-USB or USB-C. The base component 115 shall be fully customizable as for the mechanical thread, size and other formality in order to be compatible for the variety of physical interfaces of a gas regulating apparatus.

Figure 2A:
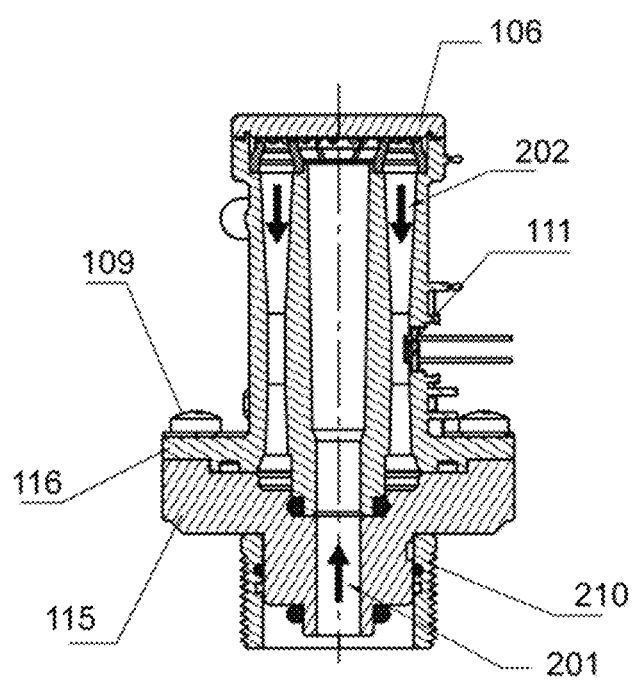
FIG. 2A is a cross section view of the MEMS mass flow meter metrology unit that can be scaled or tailored to different full scale for the desired metrology requirements to match for the variety of the gas regulating apparatus configurations.
Figure 2B:
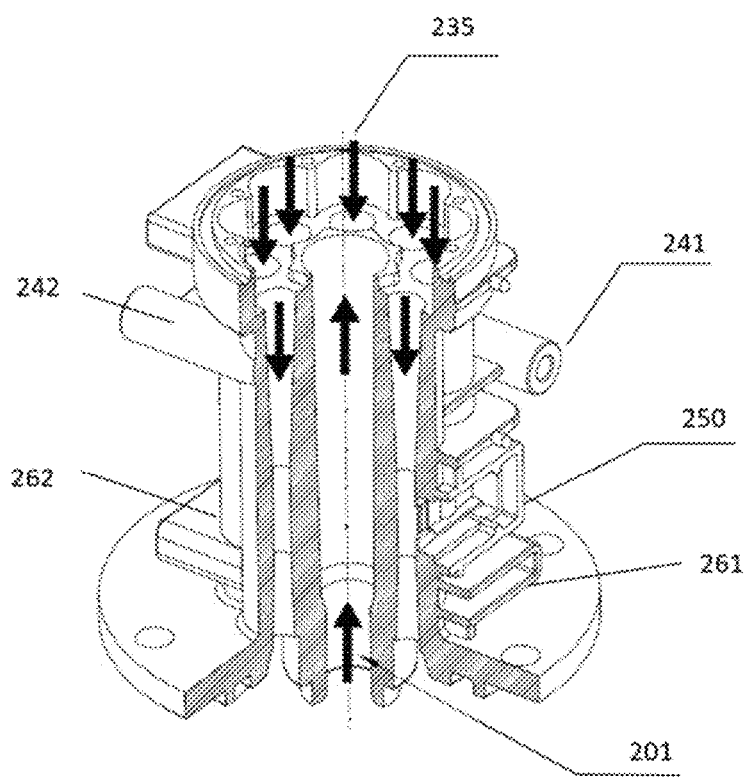
FIG. 2B is the 3D view with opening that disclosed the structure for the arrangement of the flow paths that allow the even distribution and partition of the flow as Weil as example of the placement for the mass flow sensor including installation fixtures.
Figure 2C:
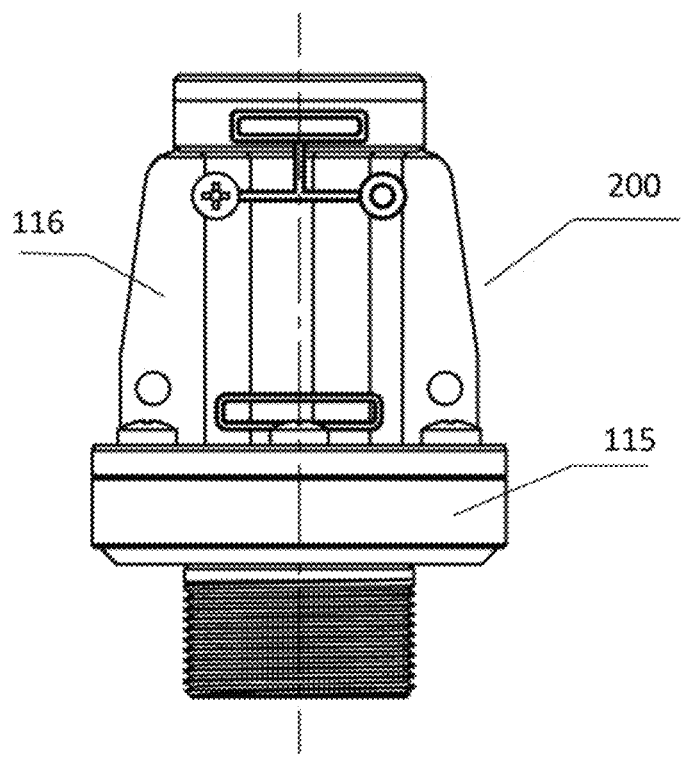
FIG. 2C is an example of the fully assembled metrology unit of the said MEMS mass flow meter.

For the preferred embodiments, the gas dispensing flow rate sensing unit 116 shall be an independent unit and shall be exchangeable with respect to the complete meter. The said unit shall be able to be adjusted as for the full scale flow rate, physical interface dimensions and wetted materials per the actual application requirements. In the preferred embodiment, FIG. 2A shows the cross section of the unit 116 where gas inlet 201 connected to the said gas regulating apparatus after the pressure regulating valve and gas flows in to the unit where the inlet flow channel is at the center of the unit from bottom up. While the top of the unit is sealed by the top cover 106, the gas flowing from the bottom is re-partitioned at the top and redistributed from the side channels 202 which are preferably to be in a form of a venturi structure in which one of the channel shall accommodate the MEMS mass flow sensor 111 at the throat of the venturi structure for the ultimate flow stability. The multiple numbers of screws 109 fix the gas dispensing flow rate sensing unit 116 to the base unit 115 where outlet channels are connected to the side channels 202. To be more explicit, FIG. 2B exhibits the detailed 3-dimensional view of the structure of the flow paths inside the gas dispensing flow rate sensing unit 116 where the plurality of numbers of the side gas re-partition channels shall be any ones depending on the required full scale flow rate or the totalized volume of gases to be dispensed at a pre-determined time period. In a preferred embodiment for cost effective manufacture, the channels shall be made symmetrically in, the circular with respect to the central gas inlet. The numbers of the side channels are preferably to be eight, and when a smaller full scale flow rate is required, some of the eight channels can be sealed or blocked based on the calculation of the reduction in the maximum flow rate. The MEMS flow sensor chamber 250, where the MEMS flow sensor is placed to measure the actual flow rate inside the channel, can be placed in any one of the eight chambers and for reliability purpose, two channels may host one MEMS sensor each. The fixtures 241, 242, 261 and 262 are made for the connection of the front 101, back 118 cover of the said mass flow meter as well as to fix the central electronic control unit 105. The final assembled gas dispensing flow rate sensing unit attached to the base is exhibited in FIG. 2C which shall be a stand-alone unit 200 that can be independently calibrated and the materials can also be altered for the gas wetted materials requirements for the desired or specific applications. The base mechanical thread and size shall also be adjustable based on the compatibility to the specific gas regulating apparatus.

Figure 3A:
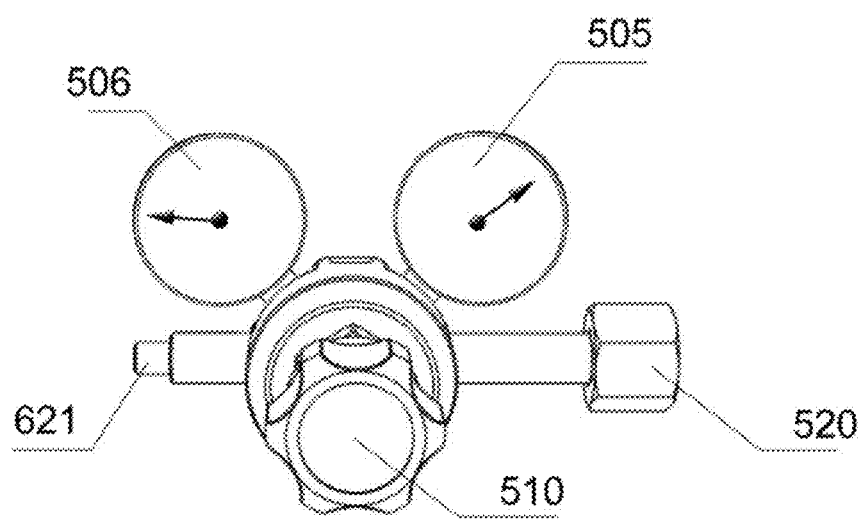
FIG. 3A is a typical mechanical regulated gas dispense apparatus.
Figure 3B:
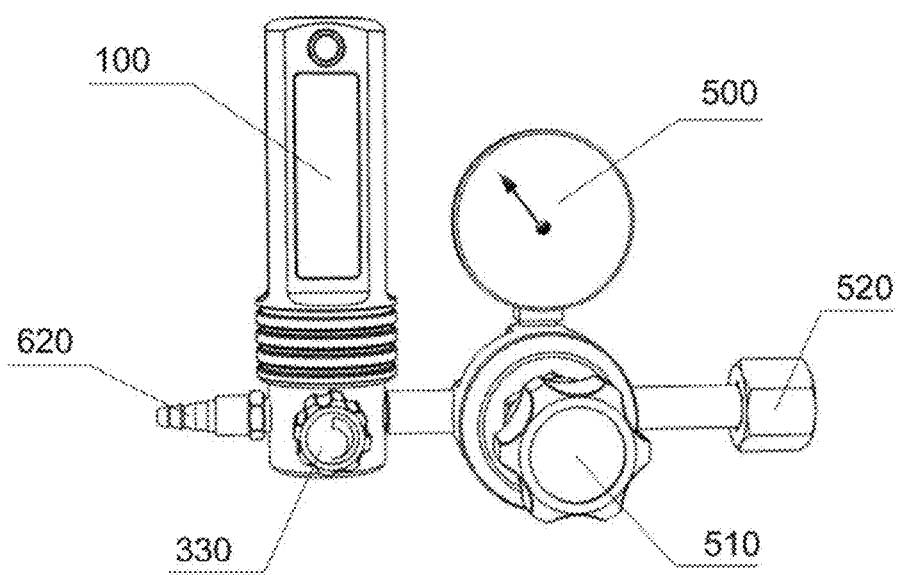
FIG. 3B is an example of the disclosed regulated digital gas dispense apparatus having the MEMS mass flow meter to register and communicate the status of the dispensed gas.

The typical current regulated gas dispense apparatus is exhibited in FIG. 3A where two mechanical pressure gauges are used to indicate the gas status inside a gas container or at the gas supply source and the pressure at the gas dispense line. In most cases, the mechanical pressure gauge 505 is a high pressure gauge that monitors the status of the pressurized gas in the bottle or cylinder or container via the connecting line 520 while the mechanical pressure gauge 506 is a low pressure gauge that monitors the gas status in the dispensing line 621 where the change in pressure is realized via the mechanical gas regulating or reducing valve 510. As the mechanical pressure gauge has a very rough resolution and low sensitivity, the status of the gas via the pressure gauges would also an estimation only resulting from time to time that the actual status is far off from what the pressure gauge indicated. The mechanical pressure gauges would obviously not be able to sending any data or perform any totalized dispensing measurement. Therefore the preferred embodiment of a regulated digital gas dispense apparatus is exhibited in FIG. 3B. The said MEMS mass flow meter 100 is used to replace the low pressure gauge that monitor the gas status in the dispense line while the high pressure gauge 500 and gas pressure regulating valve 510 are kept in case for a safe gas dispense when the gas supply is from a pressurized source such as a gas cylinder. The said mass flow meter is connected to the outlet of the manual gas regulating valve 510 and the outlet 620 is to be connected to the gas dispense line. This configuration forms the disclosed complete regulated digital gas dispense apparatus. The said mass flow meter shall be able to continuously and precisely measure the gas dispensing flow rate as well as the totalized the dispensed volume while it also provides the data streaming capability to both the users and to the third party of interest such as the bottled gas manufacturer. The additional manual regulating valve 330 shall provide additional regulation for a constant flow rate gas dispense. Other detailed functions have been discussed in the previous stated preferred embodiments that exhibit the disclosed regulated digital gas dispense apparatus shall provide a value tool to not only assist the user to timely understand the status of the bottled gas for dispensing but enables the third party such as the gas manufacturers to timely manage their m EMU Facture and control the inventory.

Figure 4A:
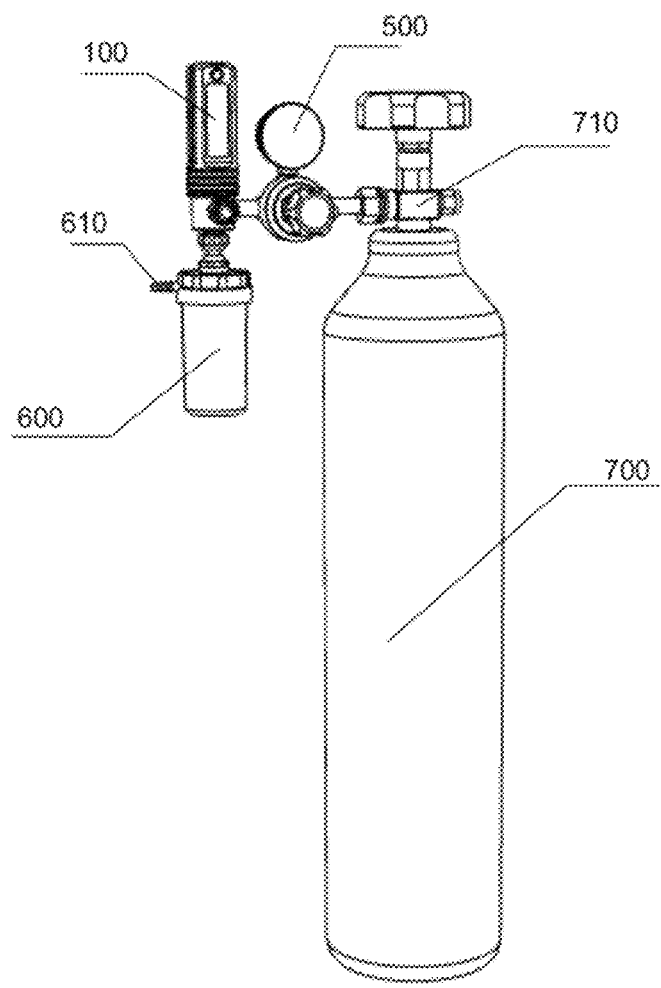
FIG. 4A is an example of the disclosed regulated digital gas dispense apparatus installed on a gas bottle or container for medical oxygen dispensing application.
Figure 4B:
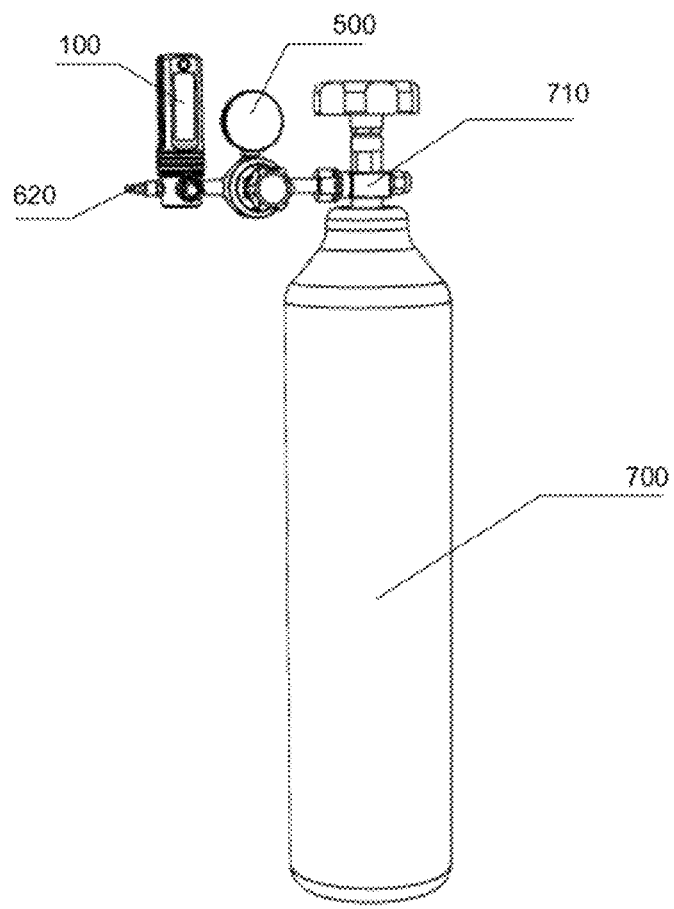
FIG. 4B is an example of the disclosed regulated digital gas dispense apparatus installed on a gas bottle or container for industrial gas dispensing applications.

To further elaborate the advantages of the above preferred embodiments, FIG. 4A and FIG. 4B exhibit two typical cases where a medical oxygen and an industrial gas dispensing applications. In the preferred embodiment for the medical oxygen gas dispensing via the bottled gas 700 (FIG. 4A), the disclosed regulated digital gas dispensing apparatus with the said MEMS mass flow meter 100 is connected to the gas bottle or cylinder via the bottle gas outlet to the valve on the bottle or cylinder 710 with the manual gas pressure regulating valve and a mechanical pressure gauge 500 to monitor the status of the gas in the bottle or cylinder whereas the said mass flow meter shall be used to continuously and precisely measure the gas dispensing flow rate and totalized volume with the data instantly streaming to the user and the third party of interest. The outlet of the said regulated digital gas dispense apparatus with the said MEMS mass flow meter 100 is connected to a humidifier 600 or a cup with hygienic water to convert the dry oxygen into wet oxygen that is dispensed from outlet 610 such that the patient respiratory air way shall not be attacked by the dry oxygen. The said digital mass flow meter shall be able to meter the desired volume of the oxygen and alert the users or the third party such as a nurse to timely attend the status of dispensing or delivery. The said mass flow meter shall also totalize the volume and compared to the initial fill of the bottle or cylinder to alert the user to the third party for a timely replacement. For the preferred embodiment of an industrial gas dispense bottle as exhibited in FIG. 4B, the said digital mass flow meter shall play the similar role as that exhibited in FIG. 4A except that the humidifier shall not be required. It is critical for many of the process manufacturers that the remaining precise volume of gas in a gas cylinder shall determine the feasibility of the next process, an over estimation shall cause the incomplete process whilst an under estimation shall increase the cost of the process. Hereafter the regulated digital gas dispense apparatus shall assist the process management as well as the inventory management for the ultimate optimization of the industrial process where the gas dispensing from a bottle or cylinder is involved.

Figure 5:
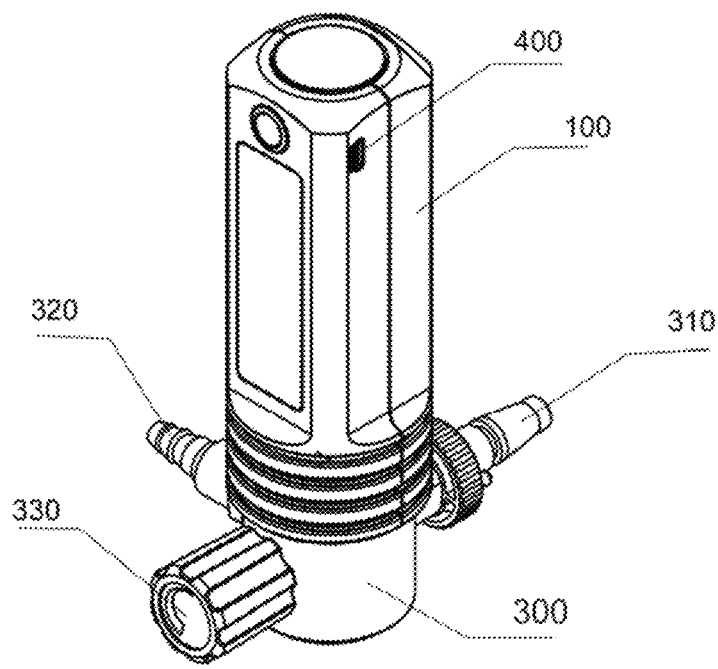
FIG. 5 is an example of the fully assembled MEMS mass flow meter installed on a meter base that contains the gas dispensing paths and the manual dispensing-control valve.

For the preferred embodiment, FIG. 5 exhibits a standalone regulated digital gas dispense apparatus with the said MEMS mass flow meter 100 that is connected to a conventional gas dispensing structure 300 where the gas inlet 310 and gas outlet 320 are 90 degree apart in the physical arrangement. A manual flow rate regulating valve 330 is used to adjust the flow speed or flow rate of the gas to be dispensed. In this preferred embodiment, the said gas dispensing regulating apparatus shall not be connected to a pressurized gas cylinder or independent gas supply but rather a non-pressurized gas supply such, as in a process line where the gas dispensing is required to be regulated to a fixed flow rate. The said mass flow meter shall be able to provide precise gas dispense without additional measurement of the pressure and temperature of the dispense line. Further it shall also relay the process data timely and remotely to the user or the third party of interest such as the control center for the intelligent management of the manufacture or process facility.

Figure 6:
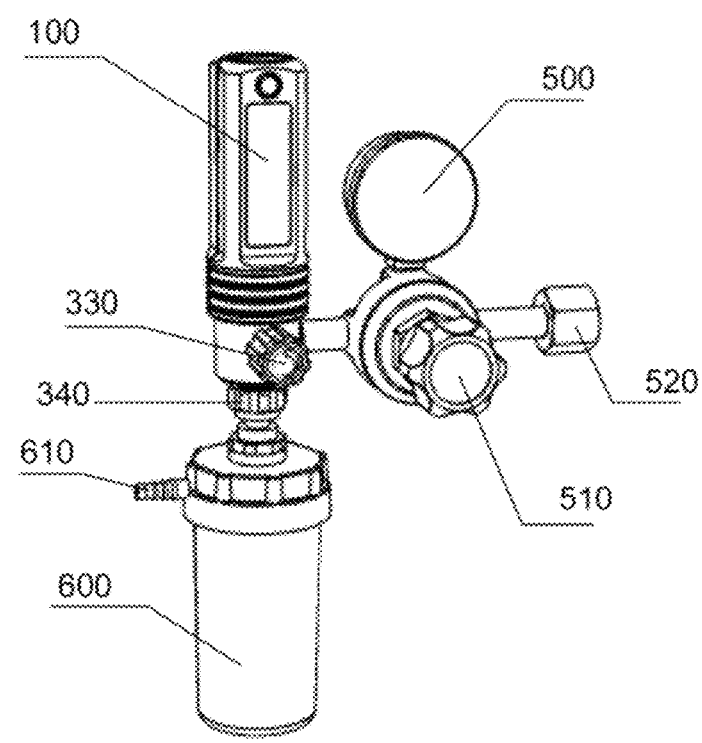
FIG. 6 is an example of the disclosed regulated digital gas dispense apparatus for medical oxygen gas from a fixed Source or oxygen gas generator.

For the preferred embodiment, FIG. 6 exhibits a standalone regulated digital gas dispense apparatus with the said MEMS mass flow meter 100 that is equipped with the high pressure gauge 500, the manual gas pressure regulating valve 510, and additional mass flow rate manual regulating valve 330. The said MEMS mass flow meter is connected via the connector 340 to a gas humidifier 600 where the gas becomes wet and dispensed via the outlet 610. In this preferred embodiment, the said gas dispensing regulating apparatus shall be able to be connected to a pressurized gas cylinder or independent gas supply. With this apparatus, the gas is regulated to a lower pressure and the said MEMS mass flow meter and the valve shall regulate the gas to be dispensed at a fixed flow rate. The said mass flow meter shall be able to provide precise gas dispense without additional measurement of the pressure and temperature of the dispense line. Further it shall also relay the process data timely and remotely to the user or the third party of interest such as the control center for the intelligent management of the manufacture or process facility.

Figure 7:
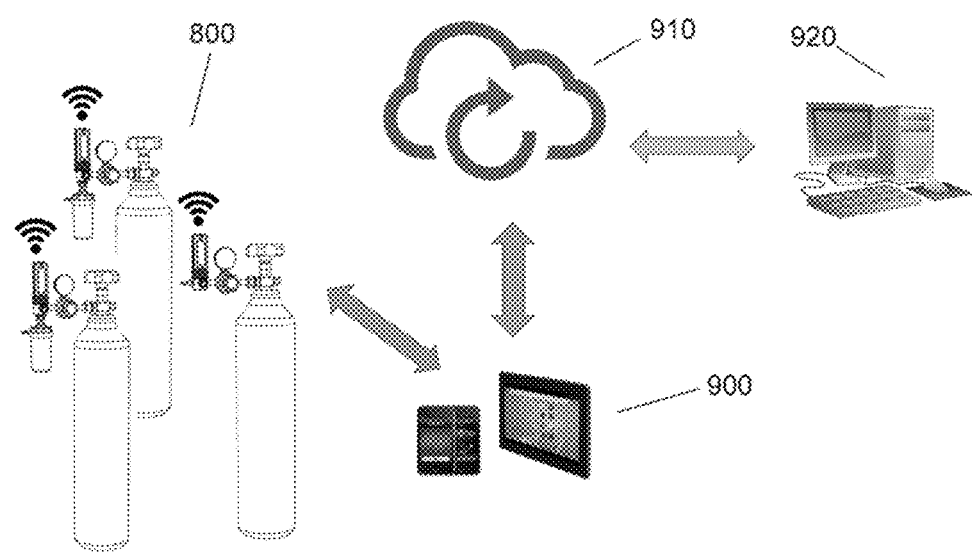
FIG. 7 is a schematic showing the component interactions in the gas management system with cloud data processing.

For the preferred embodiment, the interactions among the disclosed regulated digital gas dispense apparatus, the user with the smart devices and the cloud with data process are exhibit in FIG. 7. The regulated digital gas dispense apparatus 800 can be a single unit or a plurality of units and each of the unit shall have a unique digital address with preferred an embedded low energy Bluetooth communication chip and antenna. Each of the devices shall then communicate via the Bluetooth to the smart device 900 with streaming of the gas dispensing data that detail gas dispensing flow rate and totalized volume in each dispensing session as well as the remaining gas volume in the attached gas bottle or cylinder or container. The smart device or devices then shall stream the data up to the cloud 910 for data process 920 that can be also accessed by the user or the third party of interest for instant knowledge of the gas volume state at the each gas bottle or cylinder or container that the said regulated digital gas dispensing apparatus is attached. Alternatively, the smart device shall also instruct the said regulated digital gas dispense apparatus with an APP for various executable actions as disclosed in the previous embodiments. Further the user or the third party of interest shall also instruct the regulated digital gas dispense apparatus via the cloud and the APP on the smart device for various executable actions as disclosed in the previous embodiments.

For the additional preferred embodiment, the said regulated digital gas dispensing apparatus for those in the art shall become readily and apparently could be further incorporated with additional features such as an electrical driving valve for remote operation. It shall also be readily and apparently that the said regulated digital gas dispense apparatus shall also be equipped with other wireless communication tools such as a WIFI or even a cell data communication to interact with a local router or station for a large scale of clusters of the said gas dispensing management with the disclosed regulated digital gas dispense apparatus.

The invention claimed is:

1. A regulated digital gas dispense apparatus to replace a low pressure gas gauge and to continuously and precisely register an instant gas dispensing mass flowrate and a totally accumulated dispensed gas mass volume comprising:
   one MEMS gas mass flow sensing unit having a centralized main inlet flow channel that re-partitions a gas flow into plural side flow channels to make the side flow channels further release the gas flow into outlets;
   one MEMS mass flow sensing chip operating with calorimetric thermal mass flow sensing principle, which is placed at a side wall on one of the side flow channels; the centralized main inlet flow channel is connected to an outlet of a gas supply line or to another outlet of a manual gas pressure regulating valve; shape of the side flow channels is made into a venturi structure for flow stability; the side flow channels that re-partition the gas dispensing is in plural numbers, and at least eight of the plural side flow channels symmetrically distributed around the centralized main inlet flow channel in a circular configuration; the instant gas dispensing mass flowrate being adjusted via the numbers of the side flow channels that re-partition the flow from the centralized main inlet flow channel; diameter of each the side flow channels is identical and is from a range of 1 mm to 10 mm;
   one electronics control unit that acquires the instant gas dispensing mass flowrate and the totally accumulated dispensed gas mass volume;
   one local display that shows the instant gas dispensing mass flowrate and the accumulated dispensed gas mass volume;
   one Bluetooth Low Energy device wirelessly transmits data of the instant gas dispensing mass flowrate and the accumulated dispensed gas mass volume to a smart device;
   one physical data port is configured to download the data of the instant gas dispensing mass flowrate and the accumulated dispensed gas mass volume;
   one physical button that allows users to program a desired receiving data format which includes to allow the users to set password for data security;
   one exchangeable base which is connected with the MEMS gas mass flow sensing unit and have customized mechanical configuration to replace low pressure gauge; and
   one complete enclosure which connects components for being constituent into a complete and stand-alone mass flow meter system; wherein the enclosure meet safety requirements for medical and industrial applications; wherein the data of the instant gas dispensing mass flowrate and the accumulated dispensed gas mass volume is configured to relay to a user via a smart device having an APP connected via the embedded Bluetooth Low Energy device; wherein the data of the instant gas dispensing mass flowrate and the accumulated dispensed gas mass volume further relays to a third party of interest via data streaming to a cloud data center that enables optimized management for gas dispensing.

2. The regulated digital gas dispense apparatus of claim 1 wherein the MEMS gas mass flow sensing unit is configured to be independently calibrated; the MEMS gas mass flow sensing unit is made of plastics or other specific materials in compatible with corresponding gas wetted materials requirements.

3. The regulated digital gas dispense apparatus of claim 1 wherein numbers of the MEMS mass flow sensor chips being placed at throat of the venturi structure of the side flow channels for measurement of the instant gas dispensing mass flowrate of the dispensing gas is from 1 to 4, in consideration of reliability, performance and cost; the MEMS mass flow sensor chips are made for calorimetric thermal mass flow sensing measurement.

4. The regulated digital gas dispense apparatus of claim 1 wherein the electronics control unit have a capability to process an acquired analog instant gas dispensing mass flowrate into a digital format and the electronics control unit further totalizes the accumulated dispensed gas mass volume in each session and in consequent sessions; the electronics control unit also process the data as instructed by the users via parameters to provide all alerts whether over or under a pre-set limit of the instant gas dispensing mass flowrate and the accumulated dispensed gas mass volume; the electronics control unit communicates with a paired smart device or allows the data of instant gas dispensing mass flowrate and the accumulated dispensed gas mass volume to be downloaded and uploaded; the electronics control unit further have multiple numbers of memory chips or devices that allow the data to be simultaneously stored for a data safety; the electronics control unit also allows the user to set up password for protection.

5. The regulated digital gas dispense apparatus of claim 1 wherein the local display provides instant gas dispensing flowrate and the accumulated dispensed gas mass volume after reset of the electronics control unit; the local display also displays graphic bars that show the instant gas dispensing mass flowrate.

6. The regulated digital gas dispense apparatus of claim 1 wherein the wireless Bluetooth capability have the Bluetooth Low Energy communication device and one embedded antenna being embedded inside the electronics control unit; the Bluetooth Low Energy communication device transmit a gas dispensing data and programmed parameters to a paired smart device; the smart device is run by an APP that remotely program the electronics control unit such that a desired gas dispensing parameters program of a user is enabled or set up through the smart device with the APP which further relays the gas dispensing data to a designated cloud for cloud data processing or download an instruction from the designated cloud for the desired gas dispensing parameters program to the electronics control unit.

7. The regulated digital gas dispense apparatus of claim 1 wherein the physical data port is used to manually download the gas dispensing data as well as program any desired gas dispensing parameter via a digital data processing device; the connected digital data process device enables the data transmission to a designated cloud for further data processing; the local port is a micro- or mini-USB or USB-C port.

8. The regulated digital gas dispense apparatus of claim 1 wherein the physical button on the electronics control unit allows the user to manually set a desired gas dispensing data selected from a group consisting of alert dispense volume, alert replacement limit, alert gas dispensing flowrate, either high or low, and alert gas dispensing composition, the physical button is used for password setup for the data safety and protection.

9. The regulated digital gas dispense apparatus of claim 1 wherein the base unit is made of metal in compatible with corresponding gas wetted materials requirements.

10. The regulated digital gas dispense apparatus of claim 1 wherein the enclosure or house of the MEMS gas mass flow sensing unit is made of sturdy engineering plastics that meets the requirements of working environments and safety of the apparatus.

11. The regulated digital gas dispense apparatus of claim 1 wherein the MEMS gas mass flow sensing unit is configured to work at a low power mode and powered by a battery pack that is in compliance with industrial standard safety regulations.

12. The regulated digital gas dispense apparatus of claim 1 wherein for applications of high pressurized gas dispensing from a pressurized gas bottle or cylinder or container; the MEMS gas mass flow sensing unit replaces the mechanical low pressure gauge in a gas dispensing regulating apparatus to form a stand-alone regulated digital gas dispense apparatus with capability to relay the data to the user and to the third party of interest via a designated cloud and cloud data processing; one additional manual valve is added to the base of the MEMS gas mass flow sensing unit such that the gas dispensing flow rate is adjusted and controlled manually.

13. The regulated digital gas dispense apparatus of claim 1 wherein for applications of ambient or low pressure gas dispensing from a gas supply or fixed gas generating source, the MEMS gas mass flow sensing unit is connected to a manual valve for adjustment of the gas dispensing flowrate to form a stand-alone regulated digital gas dispense apparatus with capability to relay the data to the user and to the third party of interest via a designated cloud and cloud data processing.

14. The regulated digital gas dispense apparatus of claim 13 wherein the regulated digital gas dispense apparatus is configured to connect to a humidifier by customizing the base of the digital mass flow meter such that the regulated digital gas dispense apparatus is used for medical oxygen dispensing or delivery.

\* \* \* \* \*